United States Patent
Pirani et al.

(10) Patent No.: US 6,771,365 B1
(45) Date of Patent: Aug. 3, 2004

(54) METHOD AND DEVICE FOR DETECTING FOREIGN MATTER IN A FIBRE ASSEMBLY WHICH IS MOVED LENGTHWISE

(75) Inventors: Peter Pirani, Grut (CH); Hans Wampfler, Zurich (CH)

(73) Assignee: Uster Technologies AG, Uster (CH)

(*) Notice: Subject to any disclaimer, the term of this patent is extended or adjusted under 35 U.S.C. 154(b) by 0 days.

(21) Appl. No.: 09/979,986
(22) PCT Filed: May 22, 2000
(86) PCT No.: PCT/CH00/00285
§ 371 (c)(1),
(2), (4) Date: Dec. 31, 2001
(87) PCT Pub. No.: WO00/73771
PCT Pub. Date: Dec. 7, 2000

(30) Foreign Application Priority Data

May 29, 1999 (CH) .............................................. 1007/99

(51) Int. Cl.$^7$ .............................................. G01N 21/00
(52) U.S. Cl. .................................................. 356/238.2
(58) Field of Search ........................... 356/238.1–238.6, 356/237.1; 250/559.4, 559.41, 559.45, 221, 223 R; 340/675, 676

(56) References Cited

U.S. PATENT DOCUMENTS

| | | | |
|---|---|---|---|
| 5,414,520 A | 5/1995 | Joss et al. | |
| 5,420,439 A | 5/1995 | Landwehrkamp et al. | |
| 5,462,176 A | * 10/1995 | Hereford et al. | ............ 131/905 |
| 5,915,279 A | 6/1999 | Cantrall et al. | |

FOREIGN PATENT DOCUMENTS

| | | |
|---|---|---|
| CH | 674 379 | 5/1990 |
| DE | 297 19 245 | 4/1998 |
| EP | 0 652 432 | 5/1995 |

* cited by examiner

Primary Examiner—Tu T. Nguyen
(74) Attorney, Agent, or Firm—Burns, Doane, Swecker & Mathis, L.L.P.

(57) ABSTRACT

The invention relates to a method and a device for detecting foreign matter in a fibre composite moving in the longitudinal direction and consisting substantially of wool or cotton fibres. To provide an improved, easier and rapid method of detecting polypropylene in fibres intended for textile products the fibre composite is irradiated with infrared light (2, 3) in a defined wavelength range, the reflected light filtered (13) and the filtered fraction of the light measured (11). Values which significantly deviate from a base value indicate the presence of foreign matter.

6 Claims, 4 Drawing Sheets

METHOD AND DEVICE FOR DETECTING FOREIGN MATTER IN A FIBRE ASSEMBLY WHICH IS MOVED LENGTHWISE

The invention relates to a process and a device for detecting foreign matter in a fibre assembly which is moved lengthwise.

BACKGROUND

A process of this type and a device of this type are known from CH 674 379, in which a textile fibre material is illuminated with multicoloured or white light and an image of the yarn is produced on two sensors which are each only sensitive to one colour. The output signals of the sensors are guided onto an electronic differential circuit. Colour changes which are caused by foreign fibres in the yarn lead to a spontaneous change of the output signal from the differential circuit if the colour differs from the raw cotton.

A further process and a further device are known from EP 0 652 432. A textile fabric moved lengthwise is also illuminated here by a polychromatic light source and the reflected light is simultaneously detected on at least two wavelengths. Wavelengths in the near infrared range should also be detected in order to detect foreign matter, the colour of which differs from the basic colour of the yarn to be checked.

A disadvantage of these known processes and devices is that reliable differentiation of foreign matter such as, for example, polypropylene, is impossible in the spectral range of visible light. However, as polypropylene is very widely used as packaging material for cotton bales and the covers of the bales are not always removed with the necessary care, allowance has to be made for parts of the polypropylene covers being mixed with the cotton and appearing at any time in the processing of the cotton and being able to impair the product. Although processes are known from the plastics industry which are based on the high absorption of the C—H bond of the plastics materials, the obvious attempt to detect polypropylene in cotton, in that polypropylene is shown in cotton by absorption of the radiation at 3.43 micrometers, is inconclusive, as polypropylene and cotton both appear as dark areas. Perfect detection of polypropylene is difficult under these circumstances and can lead to false conclusions on its presence.

SUMMARY OF THE INVENTION

The invention as characterised in the claims achieves the object of providing a process and device which avoid these disadvantages and allow improved, simplified and rapid detection of polypropylene in fibres which are combined as yarn, nonwoven fabric or flocks for textile products.

This is achieved in that the reflection with different strengths of fibres made of cotton, wool, etc. and of foreign matter such as, for example, polypropylene is deliberately exploited. We refer here to the reflection of beams on the actual basic materials of which the fibre assembly on the one hand and the foreign matter on the other hand consist. This is in contrast to known processes which carry out detection on the basis of properties of additives, such as, for example, dyes. Dyes absorb and reflect in different wavelength ranges to the basic materials such as, for example, cellulose or manmade fibres such as, for example, nylon as basic material for the fibres of the fibre assembly. The invention exploits the fact that the reflection of infrared radiation by the fibres and by the foreign matter differs more in certain wavelength ranges than in other wavelength ranges. However, depending on the batch, this can have more or less success. According to the present invention it is proposed to coordinate various points of view so the desired success is achieved. Firstly, radiation should be used with at least one wavelength at which the reflection on the basic materials of the fibres and on the basic materials of the foreign matter produces values which are as different as possible to allow a good selection. Secondly, at least one wavelength of the radiation used should advantageously be selected in such a way that the fibres, which should be the basic material, carrier or a type of background for the foreign matter, reflect the radiation as little as possible or not at all. This then allows the fibre assembly and therefore the basic material to be shown against a background which is such that it does not reflect radiation of this type. With this procedure a process is obtained in which the test piece is subjected to radiation of a specific wavelength and in the process only the foreign matter, here in particular the polypropylene, appears as a light patch. In the process there can be no distinction between the background and the test piece. This means that the radiation is adapted to the basic material thereof in such a way that it absorbs this radiation and that polypropylene at least partially reflects the radiation, the background appearing identical to the basic body of the fibre assembly to the sensor, i.e. dark. This can be achieved in that, for example, the background absorbs the radiation in an absorber, or reflects or diffuses it. An optical element, for example a dielectric filter, the reflection of which has been adapted, can also be used as a background.

In brief, the fibre assembly should be subjected to infrared radiation and the reflected radiation should be measured from a limited wavelength range, values which substantially differ from a basic value indicating a foreign matter. The limited wavelength range can be produced by filtering the radiation or directly by a suitable radiation source. The limited wavelength should be adapted to an absorption band of the basic material, for example to cellulose in the case of natural fibres. An absorption band around a wavelength of approximately 2.95 micrometers is particularly favourable, as cellulose absorbs in this range. In this range, cellulose appears "black" and the background can easily be adapted as is necessary for the independence of the measurement from the diameter of the fibre assembly. Two wavelengths can also be selected which are adapted to the basic material of the fibres and the foreign matter in such a way that the foreign matter becomes noticeable in different ways in the two wavelengths.

The device according to the invention therefore has a suitable radiation source, a means for limiting the wavelength range and a detector. A means of this type is, for example, a filter which separates those portions of the radiation which have an undesired wavelength. An image-forming system can be, but need not be provided. A circuit for evaluating the signal emitted by the detector is connected thereto.

In a particular embodiment, the process according to the invention can be designed in such a way that the reflected radiation is divided into at least two beams and is filtered, the filtered portion being measured for each beam and the measured values related to one another or compared to indicate foreign matter.

The advantages achieved by the invention are in particular, that a signal which is to be unambiguously interpreted is produced thereby and reliably indicates whether there is any foreign matter of this type present or not. The invention also allows the process to be used in various wavelengths and two signals to be produced in this way which then indicate foreign matter if both suggest the same conclusion. Measurement in two wavelengths also allows foreign matter to be detected without adaptation of the background to the test piece. If adaptation is possible in the two wavelengths, this can be an advantage. Therefore, a large difference in the quantity of reflected radiation in the ranges of a single wavelength and a smaller or opposite difference in the ranges of other wavelengths can be compared and exploited in such a way that a definite statement is also possible. A further advantage is that the device can be constructed from components which are known per se and commercially available. As neither the dye nor an additive to the basic material is to be detected, there is no false indication of defects in the case of vegetable foreign matter or impurities if, in the case of vegetable matter and natural fibres, the basic material which is to react to the radiation is the same.

With this process and device foreign matter or impurities may be detected in different types of fibre assemblies such as slivers, webs, flakes and so on.

BRIEF DESCRIPTION OF THE DRAWINGS

The invention will be described in more detail hereinafter with the aid of an embodiment and with reference to the accompanying drawings, in which.

DETAILED DESCRIPTION OF PREFERRED EMBODIMENTS OF THE INVENTION

Figure 1:
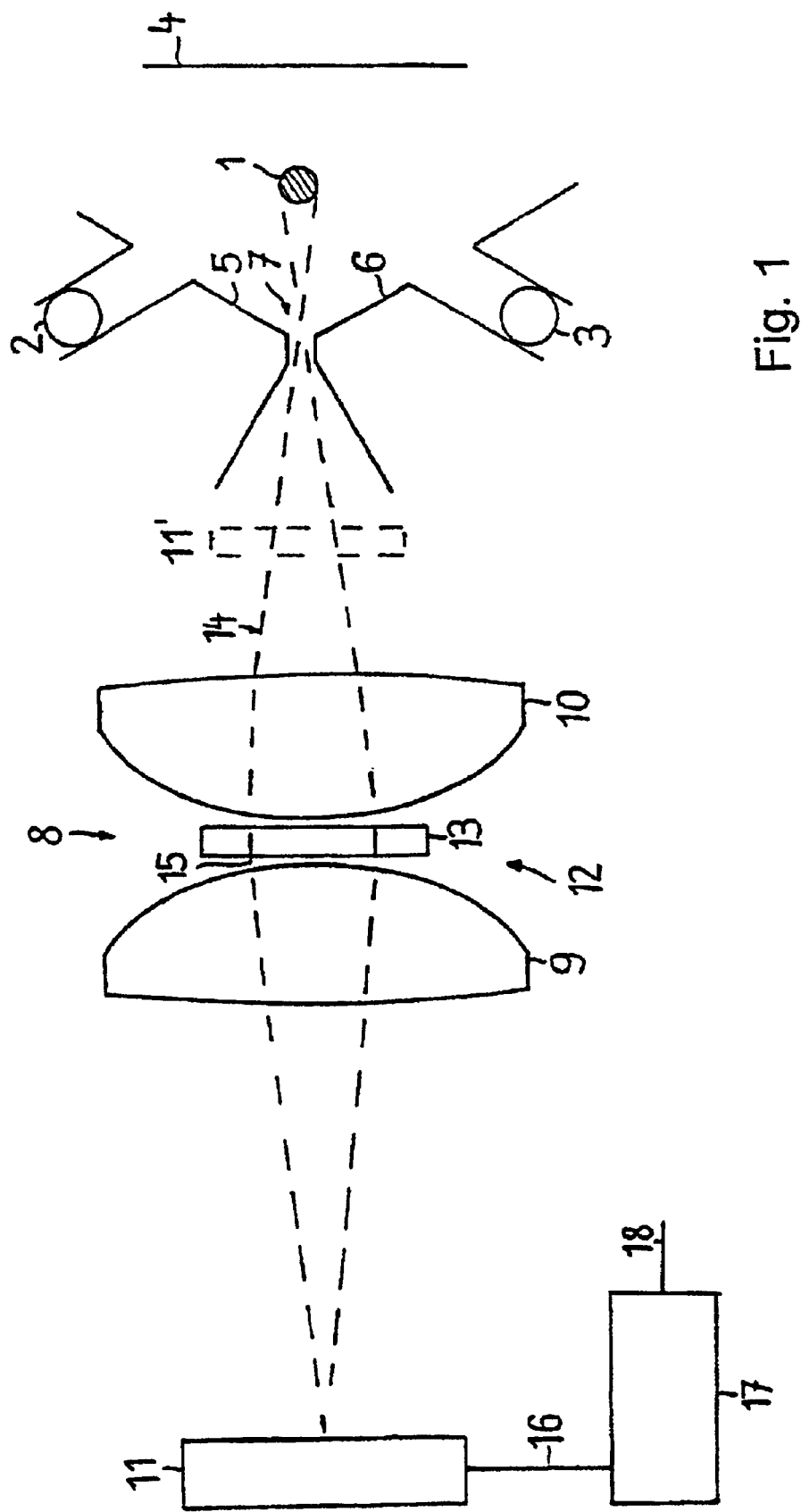
FIG. 1 is a schematic view of a first embodiment of the device according to the invention.

FIG. 1 shows a fibre assembly 1, shown as a yarn here, and two radiation sources 2, 3 to which the fibre assembly 1 is subjected in front of a background 4, but which do not directly irradiate the background 4 immediately behind the fibre assembly 1. Limiting elements 5, 6 together form an aperture plate 7 which allows radiation 14 reflected from the fibre assembly 1 to enter an image-forming system 8. This image-forming system consists of two lenses 9, 10 which direct and concentrate the beams 14 onto a sensor 11. The lenses 9, 10 produce beams 15 which run parallel in an interstice 12, so a filter 13 which works with the parallel beams 15 can be arranged there. The beams relayed from the filter 13 strike the sensor 11 which, via a line 16, can emit a signal which depends on the intensity of the impinging beams and, for example, is proportional to this intensity. An evaluation unit 17 which has an output 18 can be connected via the line 16 to the sensor 11. However, it is also possible to provide a sensor 11' with integrated filter, for example directly behind the aperture plate 7 and to provide no image-forming system. Otherwise, a sensor 11, 11' can be designed without an integrated filter and the filter can be arranged directly downstream of the radiation source. A narrow-band radiation source, for example an LED, can also be used, however.

FIG. 2 again shows the elements which are already known from FIG. 1 and which are therefore provided with the same reference numerals. However, a beam splitter 19 is used here between the sensor 11 and the lens 9. This deflects the received beams additionally onto a sensor 21, so an additional beam path 20 is also produced. A filter 28, 29 is placed upstream of each sensor 11 and 21. The sensor 21 is also connected to the evaluation unit 17 via a line 22. The background 4 can also be designed as an absorber, or have an absorber 45.

Figure 3:
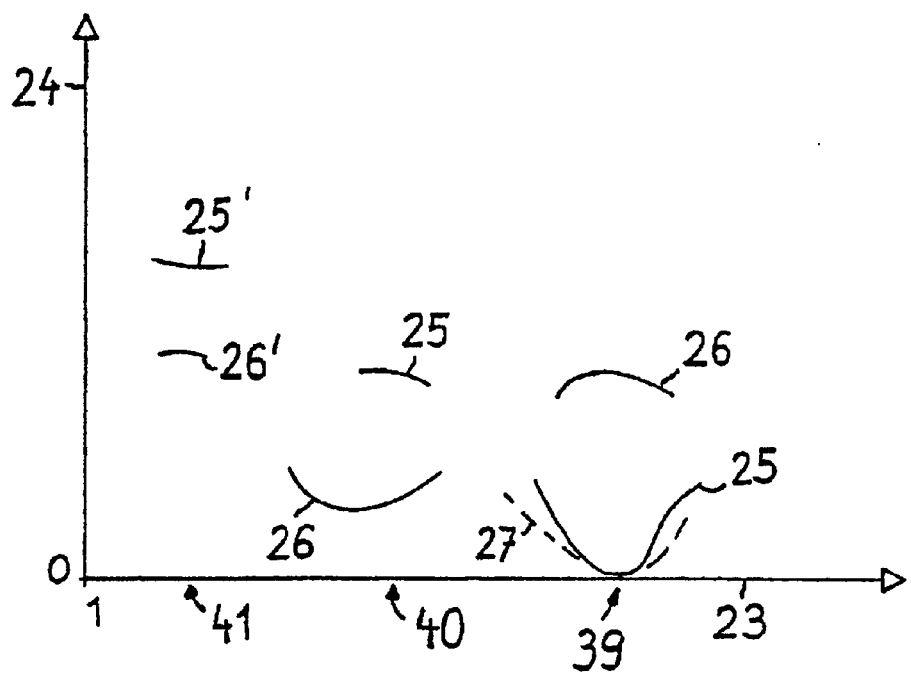
FIG. 3 is a view of the reflection behaviour of fibres and foreign matter.

FIG. 3 shows the reflection coefficient of fibre material as a function of the impinging radiation. Therefore, plotted along the horizontal axis 23 are values for wavelengths and along the vertical axis 24 values for the reflection coefficient. Curves for the reflection coefficient of cotton are plotted at 25, polypropylene at 26 and wool at 27.

Figure 4:
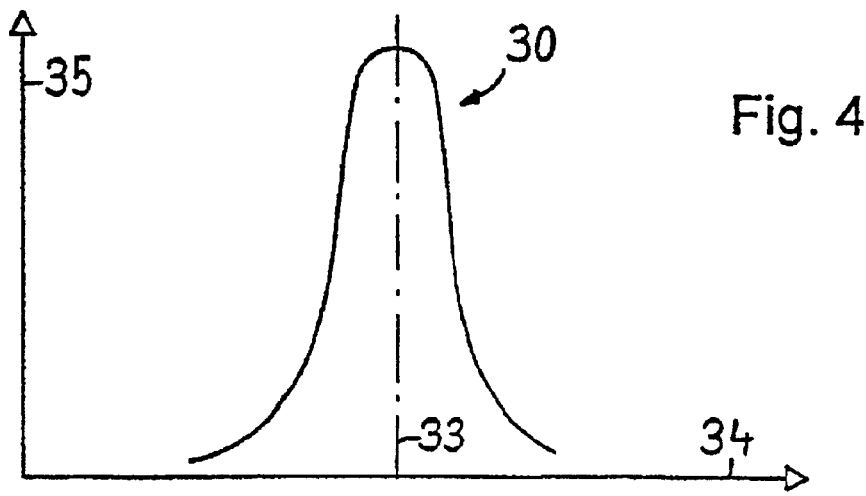
FIG. 4 is a schematic view of the characteristics of a filter used in the device and FIG. 5 shows possible courses of output signals.

FIG. 4 shows a filter characteristic 30 which is advantageous for the design of the band-pass filter 13, 28 and 29. The width of this curve and therefore of the spectral reflection behaviour of the filter should be adapted to the spectral reflection characteristics of the yarn in such a way that, on the one hand, as much signal as possible comes through and, on the other hand, only those wavelengths are allowed through which have suitable reflection. Optimization can be computed after measuring the reflection as a function of the wavelength. Values for wavelengths are therefore provided along a horizontal axis 34 and values for the transmission of the radiation are provided along a vertical axis 35.

Figure 5:
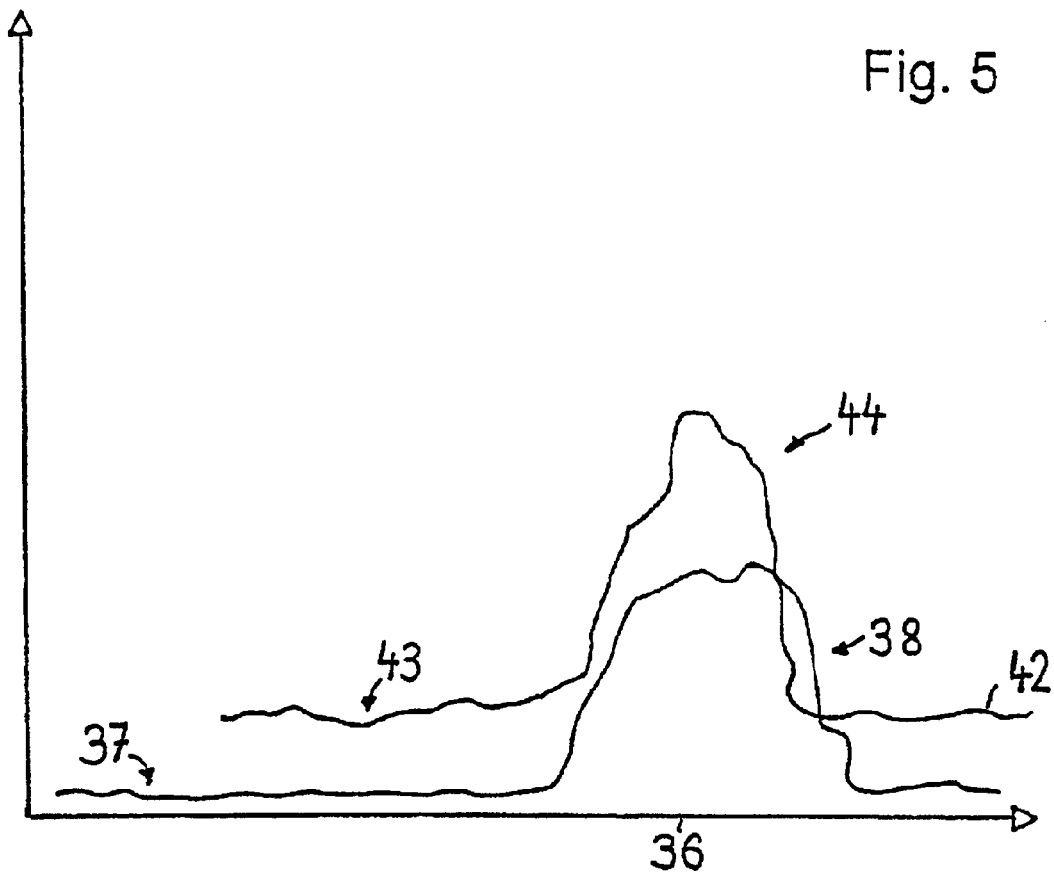

FIG. 5 shows an example for values which can occur at the outlet 18 of the evaluation unit 17 or in lines 16, 22 at the outlet of a sensor. Values are plotted here over a time axis 36 for the radiation intensity, measured in the sensor, of the radiation reflected on the fibre assembly. In a region 37 corresponding to the pure fibre material, there is hardly any reflection of radiation, in contrast to a region 38, so a signal occurs here and indicates a foreign matter which responds to the radiation.

Figure 6:
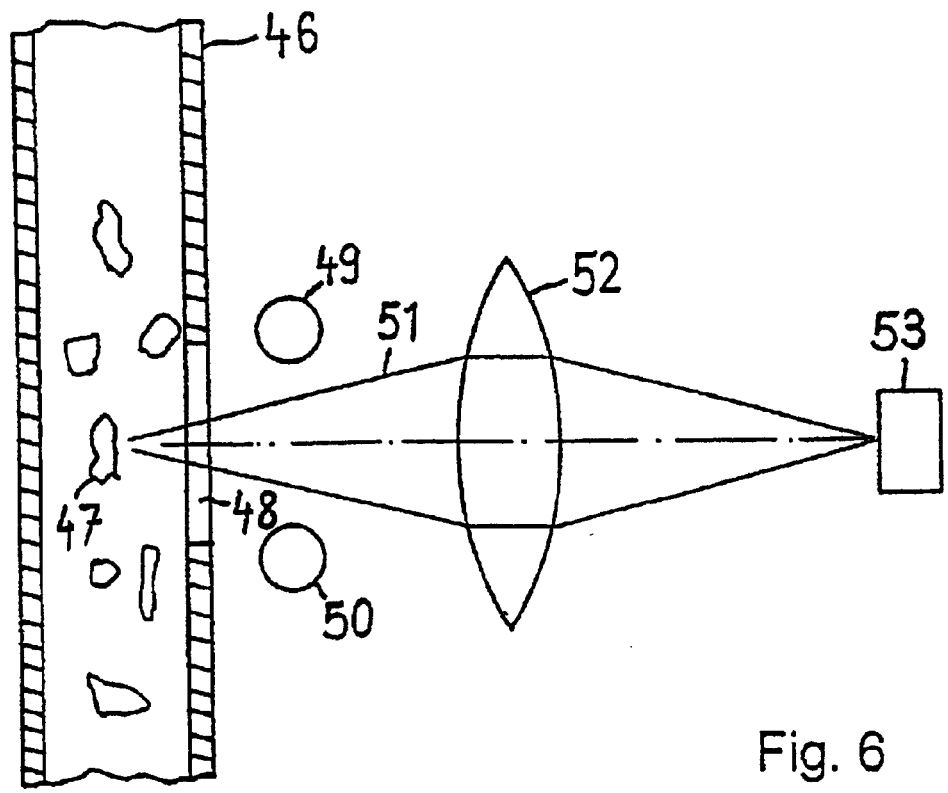
FIG. 6 shows a further embodiment of a device according to the invention.

FIG. 6 shows an example of an embodiment which permits to detect impurities in a stream of flocks composed of fibres. Therefore, a channel 46 is provided for a fluid flow which moves flocks 47. Next to a window 48 in channel 46 sources of radiation 49, 50 are placed which direct radiation onto the flocks 47 through window 48. Radiation 51 reflected by the flocks 47 is received by an imaging system 52 and thereby directed to a detector 53. Sources of radiation 49, 50 preferably provide infrared radiation. That means, that window 48 may transmit infrared radiation.

The mode of operation of the invention is as follows:

The fibre assembly 1 is moved in its lengthwise direction in the device according to FIG. 1 perpendicularly to the plane of the drawing. In the process, it can also move slightly in a direction which lies in the plane of the drawing. In the process, it is irradiated from one side by the radiation sources 2, 3, the radiation impinging on the fibre assembly 1. Reflected radiation is laterally limited by the aperture plate 7 and guided onto the lenses 10, 11, also traversing the filter 13. In this filter 13, those portions of the radiation which have undesired frequencies are filtered out and only frequency contents corresponding to the characteristics according to FIG. 4 pass through and, in a concentrated fashion, reach the sensor 11. The sensor 11 only produces a signal in the line 16 when radiation has traversed the filter 13, which is only the case when radiation is reflected on the fibre assembly 1. If the main axis 33 of the filter 13 is adjusted to approximately 2.95 micrometers, a region 39 is arrived at according to the curve 25 from FIG. 3, in which region 39 the fibre assembly, like the cotton here, absorbs practically all the radiation and therefore does not emit any radiation, and this gives a basic value. A measured value output by the sensor 11 is at least approximately zero in this case. If the background 4 is created in such a way that it is adapted to the test piece, it emits practically no signal during measurement and the cotton or pure fibre assembly cannot be differentiated from the background 4 on the basis of the measured values. This can be achieved, for example in that the background 4 is black, i.e. absorbs or diffuses radiation or also consists of cotton or the same fibre material. At the point 39 of the curve 25 in FIG. 3 it can be seen that the curve 26 differs substantially from zero and that the foreign material, like the polypropylene here, reflects radiation. It is therefore this radiation which can traverse the band-pass filter 13 and be detected in the sensor 11. This case is shown by the regions 37 and 38 of a curve in FIG. 5. As shown by the curves 25 and 26 in FIG. 3, a positive difference is produced between the reflection coefficients of the foreign matter and the fibres in the fibre assembly 1 which is expressed in region 38 from FIG. 5.

Figure 2:
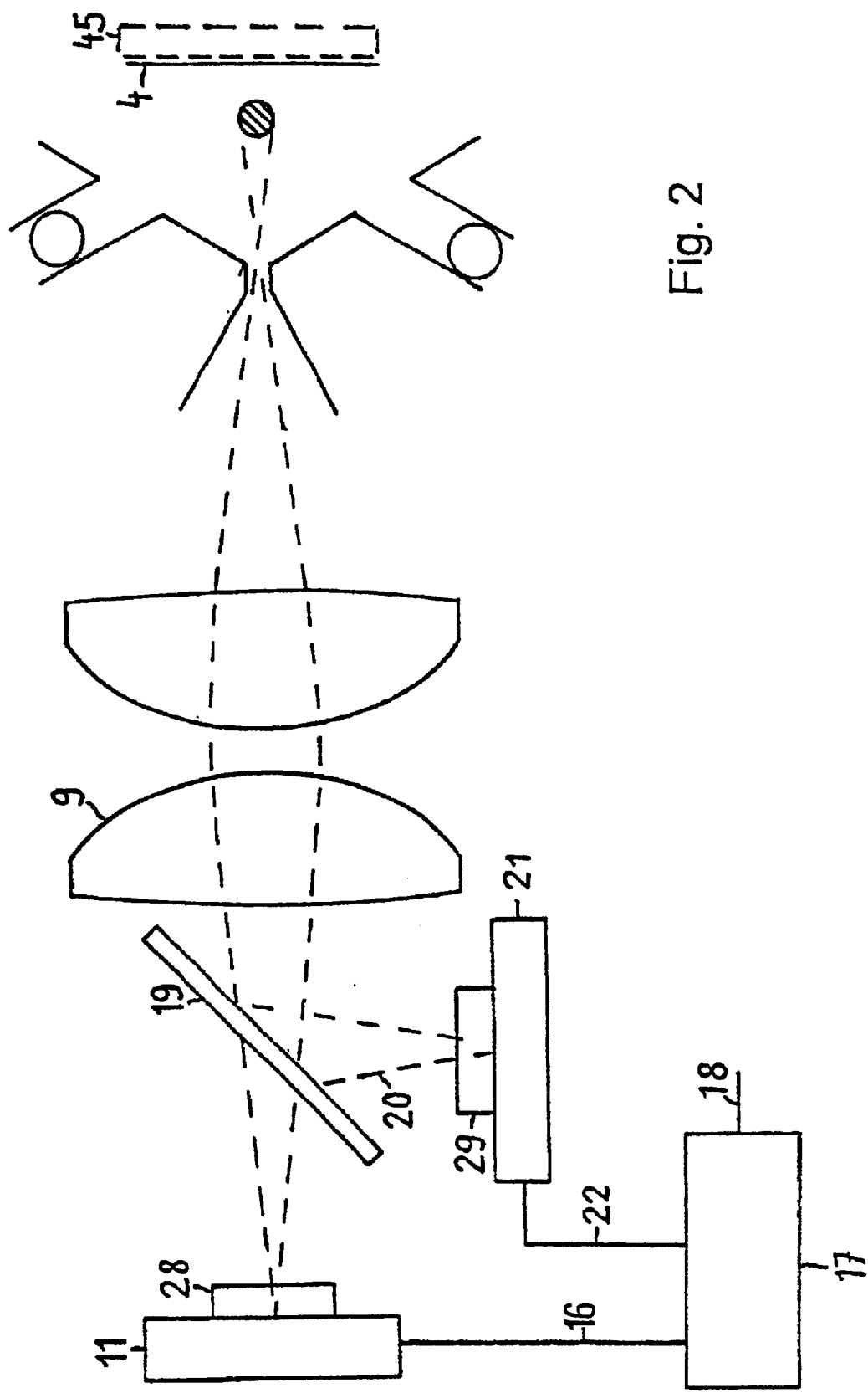
FIG. 2 is a schematic view of a second embodiment of the device according to the invention.

If the embodiment according to FIG. 2 is used, the reflected radiation is filtered in two different filters 28, 29 and detected in sensors 11, 21 and this occurs simultaneously and therefore concerns the same point, for example on the current fibre assembly. With this device the filter 28, for example, could have aligned its main axis 33 to a wavelength of about 2.3 micrometers and the filter 29 its main axis 33 to about 1.5 micrometers. According to FIG. 3, points 40 and 41 are being worked with, for example. At both points 40 and 41 substantial differences between the reflection coefficients of the fibres and the foreign matter are detected. However, the fibres 1 also reflect radiation which impinges on the sensors 11 and 21. There can also be cases in which the fibre assembly 1 reflects more than the foreign matter depending on the wavelength range. The evaluation unit 17 continuously compares the signals of the values of the radiation detected in the sensors 11 and 21 to form a final value. As long as only fibre material is present and no foreign matter, this comparison produces for example the difference between the values which were measured at points 40 and 41 according to the two curves 26, 26' as shown in FIG. 3. This can already produce an output signal according to a curve 42, the portion 43 of which gives a basic value. With incomplete adaptation of the background to the basic material in one or both wavelengths, the signal is also influenced by density changes, diameter changes or position changes of the fibre assembly 1. By comparing the two signals from the sensors 11 and 21, the influences of the density changes, diameter changes or also position changes of the fibre assembly 1 can be differentiated from a real foreign matter signal. This process can be carried out, for example, at wavelengths such as 2.95 and 2.35, 1.5 and 1.7, 1.5 and 1.2 micrometers or at other combinations of these values.

When using two wavelengths in which the sensor receives a reflection signal from the test piece, for example the cotton or wool, and therefore detects these, either the reflection properties of the background can be adapted to that of the cotton or to the wool at both wavelengths. Two signals are then received which are independent of diameter and each of the two independently indicate polypropylene. The evaluation of the two signals gives more reliability. On the other hand, if there is no optimum adaptation to the background in the two wavelengths, the diameter can theoretically be precisely compensated by evaluation of the signals. However, it is sufficient that, owing to the "contrast reversal", (sometimes the cotton is lighter than the propylene, sometimes the reverse) the signals go in different directions when polypropylene is present, whereas they go in the same direction in the case of thickness variations in the yarn. The diameter is therefore not completely and precisely compensated, but essentially the sign of the signals is used to differentiate between diameter variations and foreign matter.

The principle of this process is that the fibre assembly should be detected in wavelength ranges in which the fibre assembly or the foreign matter should absorb as much radiation as possible, while the foreign matter or the fibre assembly should, on the contrary, absorb as little radiation as possible. Therefore the fibre assembly produces only a weak signal in one case, but the foreign matter produces a comparatively strong signal or vice versa. This has the advantage that it is not important how strongly the fibre assembly stands out from the background and therefore it is not problematic if the fibre assembly changes in density or thickness.

As a source of radiation, so-called incandescent microlamps can be used, for example, which have a lead glass cover. This guarantees that the radiated spectrum contains a sufficient infrared content.

Possible sensors are, for example, photoconductive lead salt detectors. However, they also have a 1/f noise, also called flicker noise. The volume of this is inversely proportional to the frequency. Therefore low frequency signals have to be filtered out. Another embodiment could consist of a conventional commercial infrared camera, for example a line array or an FPA (focal plane array) with an upstream band-pass filter, preferably set to 2.95 micrometers. A beam splitter with a diffuser is necessary.

What is claimed is:

1. A method for detecting the presence of foreign matter in association with fibres being moved past a detection station, said method comprising:

exposing the fibres to infrared radiation as they pass the detection station, said infrared radiation including a limited wavelength range that is substantially absorbed by the fibres and is reflected by the foreign matter, and measuring the reflected radiation in said limited wavelength range as the fibres move past said detection station, such that a substantial increase in the reflected radiation measurement value indicates the passage of foreign matter.

2. A method according to claim 1, including filtering the radiation reflected from said detection station to filter out wavelengths other than those in a limited wavelength range centered around a wavelength of about 2.95 micrometers.

3. A method according to claim 2, wherein a background for the moving fibres also is exposed to said infrared radiation and wherein said background substantially absorbs radiation in said limited wavelength range.

4. A method according to claim 1, wherein a background for the moving fibres also is exposed to said infrared radiation and wherein said background substantially absorbs radiation in said limited wavelength range.

5. A method for detecting the presence of foreign matter in association with fibres being moved past a detection station, said method comprising:

exposing the fibres to infrared radiation as they move past said detection station, said infrared radiation including a first limited wavelength range that is absorbed more by the basic material of the fibres than by the basic material of the foreign matter, and a second limited wavelength range that is different from said first wavelength range and that is absorbed differently by the basic material of said fibres and the basic material of said foreign matter;

measuring the radiation in said first limited wavelength range which is reflected from said detection station;

separately measuring the radiation in said second limited wavelength range which is reflected from said detection station; and comparing the measured reflected radiation values to provide an indication of the presence or absence of foreign matter in the material passing the detection station.

6. A method according to claim 5, wherein infrared radiation in said second limited wavelength range is absorbed more by the basic material of said foreign matter than by the basic material of said fibres.

* * * * *